(12) United States Patent
Hajishah et al.

(10) Patent No.: US 9,795,507 B2
(45) Date of Patent: Oct. 24, 2017

(54) MULTIFUNCTION FOOT PEDAL

(71) Applicant: Abbott Medical Optics Inc., Santa Ana, CA (US)

(72) Inventors: Abraham Hajishah, Irvine, CA (US); Mitchell W. Mallough, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 576 days.

(21) Appl. No.: 14/531,151

(22) Filed: Nov. 3, 2014

(65) Prior Publication Data

US 2015/0051607 A1    Feb. 19, 2015
US 2017/0128264 A9    May 11, 2017

Related U.S. Application Data

(63) Continuation-in-part of application No. 12/613,591, filed on Nov. 6, 2009.

(60) Provisional application No. 61/112,517, filed on Nov. 7, 2008, provisional application No. 61/983,324, filed on Apr. 23, 2014.

(51) Int. Cl.
*G05G 1/44* (2008.04)
*A61F 9/007* (2006.01)

(52) U.S. Cl.
CPC ........... *A61F 9/00745* (2013.01); *G05G 1/44* (2013.01)

(58) Field of Classification Search
None
See application file for complete search history.

(56) References Cited

U.S. PATENT DOCUMENTS

| | | |
|---|---|---|
| 1,848,024 A | 3/1932 | Owen |
| 2,123,781 A | 7/1938 | Huber |
| 2,990,616 A | 7/1961 | Balamuth et al. |
| 3,076,904 A | 2/1963 | Claus |
| 3,116,697 A | 1/1964 | Bilichniansky |
| 3,439,680 A | 4/1969 | Thomas, Jr. |
| 3,526,219 A | 9/1970 | Lewis |
| 3,781,142 A | 12/1973 | Zweig |
| 3,857,387 A | 12/1974 | Shock |
| 4,017,828 A | 4/1977 | Watanabe et al. |

(Continued)

FOREIGN PATENT DOCUMENTS

| | | |
|---|---|---|
| AU | 2006235983 A1 | 5/2007 |
| DE | 3826414 A1 | 2/1989 |

(Continued)

OTHER PUBLICATIONS

International Search Report and Written Opinion for Application No. PCT/US2015/058655, dated Jan. 28, 2016, 13 pages.

(Continued)

*Primary Examiner* — Isaac T Tecklu
(74) *Attorney, Agent, or Firm* — Abbott Medical Optics Inc.

(57) ABSTRACT

A foot pedal with a treadle that pivots up and down to vary its pitch, and/or side to side to vary its yaw. The pivot range of motion is divided into a plurality of zones, each zone configured to correspond to a respective virtual switch. When the treadle is pivoted into one of the zones, the corresponding virtual switch is activated. The virtual switch controls an operatively coupled device such as a handpiece used in a surgical procedure.

36 Claims, 9 Drawing Sheets

(56) References Cited

U.S. PATENT DOCUMENTS

| | | |
|---|---|---|
| 4,037,491 A | 7/1977 | Newbold |
| 4,189,286 A | 2/1980 | Murry et al. |
| 4,193,004 A | 3/1980 | Lobdell et al. |
| 4,276,023 A | 6/1981 | Phillips et al. |
| 4,537,561 A | 8/1985 | Xanthopoulos |
| 4,564,342 A | 1/1986 | Weber et al. |
| 4,590,934 A | 5/1986 | Malis et al. |
| 4,662,829 A | 5/1987 | Nehring |
| 4,665,621 A | 5/1987 | Ackerman et al. |
| 4,706,687 A | 11/1987 | Rogers et al. |
| 4,757,814 A | 7/1988 | Wang et al. |
| 4,758,220 A | 7/1988 | Sundblom et al. |
| 4,772,263 A | 9/1988 | Dorman et al. |
| 4,773,897 A | 9/1988 | Scheller et al. |
| 4,818,186 A | 4/1989 | Pastrone et al. |
| 4,837,857 A | 6/1989 | Scheller et al. |
| 4,920,336 A | 4/1990 | Meijer |
| 4,921,477 A | 5/1990 | Davis |
| 4,933,843 A | 6/1990 | Scheller et al. |
| 4,941,518 A | 7/1990 | Williams et al. |
| 4,954,960 A | 9/1990 | Lo et al. |
| 4,961,424 A | 10/1990 | Kubota et al. |
| 4,965,417 A | 10/1990 | Massie |
| 4,983,901 A | 1/1991 | Lehmer |
| 4,998,972 A | 3/1991 | Chin et al. |
| 5,006,110 A | 4/1991 | Garrison et al. |
| 5,020,535 A | 6/1991 | Parker et al. |
| 5,026,387 A | 6/1991 | Thomas |
| 5,032,939 A | 7/1991 | Mihara et al. |
| 5,039,973 A | 8/1991 | Carballo |
| 5,091,656 A | 2/1992 | Gahn |
| 5,108,367 A | 4/1992 | Epstein et al. |
| 5,110,270 A | 5/1992 | Morrick |
| 5,125,891 A | 6/1992 | Hossain et al. |
| 5,160,317 A | 11/1992 | Costin |
| 5,195,960 A | 3/1993 | Hossain et al. |
| 5,195,961 A | 3/1993 | Takahashi et al. |
| 5,195,971 A | 3/1993 | Sirhan |
| 5,230,614 A | 7/1993 | Zanger et al. |
| 5,242,404 A | 9/1993 | Conley et al. |
| 5,249,121 A | 9/1993 | Baum et al. |
| 5,268,624 A * | 12/1993 | Zanger ............... A61F 9/00745 318/551 |
| 5,271,379 A | 12/1993 | Phan et al. |
| 5,282,787 A | 2/1994 | Wortrich |
| 5,323,543 A | 6/1994 | Steen et al. |
| 5,342,293 A | 8/1994 | Zanger |
| 5,350,357 A | 9/1994 | Kamen et al. |
| 5,351,676 A | 10/1994 | Putman |
| 5,388,569 A | 2/1995 | Kepley |
| 5,454,783 A | 10/1995 | Grieshaber et al. |
| 5,464,391 A | 11/1995 | DeVale |
| 5,470,211 A | 11/1995 | Knott et al. |
| 5,470,312 A | 11/1995 | Zanger et al. |
| 5,499,969 A | 3/1996 | Beuchat et al. |
| 5,520,652 A | 5/1996 | Peterson |
| 5,533,976 A | 7/1996 | Zaleski et al. |
| 5,549,461 A | 8/1996 | Newland |
| 5,554,894 A | 9/1996 | Sepielli |
| 5,561,575 A | 10/1996 | Eways |
| 5,569,188 A | 10/1996 | MacKool |
| 5,580,347 A | 12/1996 | Reimels |
| 5,591,127 A | 1/1997 | Barwick et al. |
| 5,653,887 A | 8/1997 | Wahl et al. |
| 5,657,000 A | 8/1997 | Ellingboe |
| 5,676,530 A | 10/1997 | Nazarifar |
| 5,676,649 A | 10/1997 | Boukhny et al. |
| 5,676,650 A | 10/1997 | Grieshaber et al. |
| 5,693,020 A | 12/1997 | Rauh |
| 5,697,898 A | 12/1997 | Devine |
| 5,697,910 A | 12/1997 | Cole et al. |
| 5,700,240 A | 12/1997 | Barwick et al. |
| 5,724,264 A | 3/1998 | Rosenberg et al. |
| 5,728,130 A | 3/1998 | Ishikawa et al. |
| 5,733,256 A | 3/1998 | Costin |
| 5,745,647 A | 4/1998 | Krause |
| 5,746,713 A | 5/1998 | Hood et al. |
| 5,747,824 A | 5/1998 | Jung et al. |
| 5,777,602 A | 7/1998 | Schaller et al. |
| 5,805,998 A | 9/1998 | Kodama |
| 5,807,075 A | 9/1998 | Jacobsen et al. |
| 5,810,766 A | 9/1998 | Barnitz et al. |
| 5,830,176 A | 11/1998 | MacKool |
| 5,843,109 A | 12/1998 | Mehta et al. |
| 5,859,642 A | 1/1999 | Jones |
| 5,871,492 A | 2/1999 | Sorensen |
| 5,879,298 A | 3/1999 | Drobnitzky et al. |
| 5,883,615 A | 3/1999 | Fago et al. |
| 5,899,674 A | 5/1999 | Jung et al. |
| 5,928,257 A | 7/1999 | Kablik et al. |
| 5,938,655 A | 8/1999 | Bisch et al. |
| 5,983,749 A | 11/1999 | Holtorf |
| 6,002,484 A | 12/1999 | Rozema et al. |
| 6,024,428 A | 2/2000 | Uchikata |
| 6,028,387 A | 2/2000 | Boukhny |
| 6,062,829 A | 5/2000 | Ognier |
| 6,077,285 A | 6/2000 | Boukhny |
| 6,086,598 A | 7/2000 | Appelbaum et al. |
| 6,109,895 A | 8/2000 | Ray et al. |
| 6,117,126 A | 9/2000 | Appelbaum et al. |
| 6,139,320 A | 10/2000 | Hahn |
| 6,150,623 A | 11/2000 | Chen |
| 6,159,175 A | 12/2000 | Strukel et al. |
| 6,179,829 B1 | 1/2001 | Bisch et al. |
| 6,200,287 B1 | 3/2001 | Keller et al. |
| 6,219,032 B1 | 4/2001 | Rosenberg et al. |
| 6,251,113 B1 | 6/2001 | Appelbaum et al. |
| 6,260,434 B1 * | 7/2001 | Holtorf .................. G05G 1/30 74/478 |
| 6,360,630 B2 | 3/2002 | Holtorf |
| 6,368,269 B1 | 4/2002 | Lane |
| 6,411,062 B1 | 6/2002 | Baranowski et al. |
| 6,424,124 B2 | 7/2002 | Ichihara et al. |
| 6,436,072 B1 | 8/2002 | Kullas et al. |
| 6,452,120 B1 * | 9/2002 | Chen ....................... G05G 1/30 200/52 R |
| 6,452,123 B1 * | 9/2002 | Chen ....................... G05G 1/30 200/86.5 |
| 6,491,661 B1 | 12/2002 | Boukhny et al. |
| 6,511,454 B1 | 1/2003 | Nakao et al. |
| 6,537,445 B2 | 3/2003 | Muller |
| 6,595,948 B2 | 7/2003 | Suzuki et al. |
| 6,632,214 B2 | 10/2003 | Morgan et al. |
| 6,674,030 B2 * | 1/2004 | Chen ....................... G05G 1/30 200/61.29 |
| 6,830,555 B2 | 12/2004 | Rockley et al. |
| 6,852,092 B2 | 2/2005 | Kadziauskas et al. |
| 6,862,951 B2 | 3/2005 | Peterson et al. |
| 6,908,451 B2 | 6/2005 | Brody et al. |
| 6,962,488 B2 | 11/2005 | Davis et al. |
| 6,962,581 B2 | 11/2005 | Thoe |
| 6,986,753 B2 | 1/2006 | Bui |
| 7,011,761 B2 | 3/2006 | Muller |
| 7,012,203 B2 * | 3/2006 | Hanson .................. A61B 17/00 200/86.5 |
| 7,070,578 B2 | 7/2006 | Leukanech et al. |
| 7,073,083 B2 | 7/2006 | Litwin, Jr. et al. |
| 7,087,049 B2 | 8/2006 | Nowlin et al. |
| 7,103,344 B2 | 9/2006 | Menard |
| 7,167,723 B2 | 1/2007 | Zhang |
| 7,169,123 B2 | 1/2007 | Kadziauskas et al. |
| 7,236,766 B2 | 6/2007 | Freeburg |
| 7,236,809 B2 | 6/2007 | Fischedick et al. |
| 7,242,765 B2 | 7/2007 | Hairston |
| 7,244,240 B2 | 7/2007 | Nazarifar et al. |
| 7,289,825 B2 | 10/2007 | Fors et al. |
| 7,300,264 B2 | 11/2007 | Souza |
| 7,316,664 B2 | 1/2008 | Kadziauskas et al. |
| 7,336,976 B2 | 2/2008 | Ito |
| 7,381,917 B2 | 6/2008 | Dacquay et al. |
| 7,439,463 B2 | 10/2008 | Brenner et al. |
| 7,465,285 B2 | 12/2008 | Hutchinson et al. |
| 7,470,277 B2 | 12/2008 | Finlay et al. |
| 7,526,038 B2 | 4/2009 | McNamara |

(56) References Cited

U.S. PATENT DOCUMENTS

| | | |
|---|---|---|
| 7,591,639 B2 | 9/2009 | Kent |
| 7,731,484 B2 | 6/2010 | Yamamoto et al. |
| 7,776,006 B2 | 8/2010 | Childers et al. |
| 7,811,255 B2 | 10/2010 | Boukhny et al. |
| 7,883,521 B2 | 2/2011 | Rockley et al. |
| 7,921,017 B2 | 4/2011 | Claus et al. |
| 7,967,777 B2 | 6/2011 | Edwards et al. |
| 8,070,712 B2 | 12/2011 | Muri et al. |
| 8,075,468 B2 | 12/2011 | Min et al. |
| 2001/0023331 A1 | 9/2001 | Kanda et al. |
| 2001/0047166 A1 | 11/2001 | Wuchinich |
| 2001/0051788 A1 | 12/2001 | Paukovits et al. |
| 2002/0019215 A1 | 2/2002 | Romans |
| 2002/0019607 A1 | 2/2002 | Bui |
| 2002/0045887 A1 | 4/2002 | DeHoogh et al. |
| 2002/0070840 A1 | 6/2002 | Fischer et al. |
| 2002/0098859 A1 | 7/2002 | Murata |
| 2002/0137007 A1 | 9/2002 | Beerstecher |
| 2002/0179462 A1 | 12/2002 | Silvers |
| 2002/0183693 A1 | 12/2002 | Peterson et al. |
| 2003/0028091 A1 | 2/2003 | Simon et al. |
| 2003/0047434 A1 | 3/2003 | Hanson et al. |
| 2003/0050619 A1 | 3/2003 | Mooijman et al. |
| 2003/0073980 A1 | 4/2003 | Finlay et al. |
| 2003/0083016 A1 | 5/2003 | Evans et al. |
| 2003/0108429 A1 | 6/2003 | Angelini et al. |
| 2003/0125717 A1 | 7/2003 | Whitman |
| 2003/0224729 A1 | 12/2003 | Arnold |
| 2003/0226091 A1 | 12/2003 | Platenberg et al. |
| 2004/0035242 A1 | 2/2004 | Peterson et al. |
| 2004/0037724 A1 | 2/2004 | Haser et al. |
| 2004/0068300 A1 | 4/2004 | Kadziauskas et al. |
| 2004/0092922 A1 | 5/2004 | Kadziauskas et al. |
| 2004/0193182 A1 | 9/2004 | Yaguchi et al. |
| 2004/0212344 A1 | 10/2004 | Tamura et al. |
| 2004/0215127 A1 | 10/2004 | Kadziauskas et al. |
| 2004/0224641 A1 | 11/2004 | Sinn |
| 2004/0253129 A1 | 12/2004 | Sorensen et al. |
| 2005/0039567 A1 | 2/2005 | Peterson et al. |
| 2005/0054971 A1 | 3/2005 | Steen et al. |
| 2005/0065462 A1 | 3/2005 | Nazarifar et al. |
| 2005/0069419 A1 | 3/2005 | Cull et al. |
| 2005/0070859 A1 | 3/2005 | Cull et al. |
| 2005/0070871 A1 | 3/2005 | Lawton et al. |
| 2005/0095153 A1 | 5/2005 | Demers et al. |
| 2005/0103607 A1 | 5/2005 | Mezhinsky |
| 2005/0109595 A1 | 5/2005 | Mezhinsky et al. |
| 2005/0118048 A1 | 6/2005 | Traxinger |
| 2005/0119679 A1 | 6/2005 | Rabiner et al. |
| 2005/0130098 A1 | 6/2005 | Warner |
| 2005/0187513 A1 | 8/2005 | Rabiner et al. |
| 2005/0197131 A1 | 9/2005 | Ikegami |
| 2005/0209560 A1 | 9/2005 | Boukhny et al. |
| 2005/0236936 A1 | 10/2005 | Shiv et al. |
| 2005/0245888 A1 | 11/2005 | Cull |
| 2005/0261628 A1 | 11/2005 | Boukhny et al. |
| 2006/0035585 A1 | 2/2006 | Washiro |
| 2006/0036180 A1 | 2/2006 | Boukhny et al. |
| 2006/0041220 A1 | 2/2006 | Boukhny et al. |
| 2006/0046659 A1 | 3/2006 | Haartsen et al. |
| 2006/0074405 A1 | 4/2006 | Malackowski et al. |
| 2006/0078448 A1 | 4/2006 | Holden |
| 2006/0114175 A1* | 6/2006 | Boukhny ............ A61F 9/00745 345/24 |
| 2006/0145540 A1 | 7/2006 | Mezhinsky |
| 2006/0219049 A1 | 10/2006 | Horvath et al. |
| 2006/0219962 A1 | 10/2006 | Dancs et al. |
| 2006/0224107 A1 | 10/2006 | Claus et al. |
| 2006/0236242 A1 | 10/2006 | Boukhny et al. |
| 2007/0016174 A1 | 1/2007 | Millman et al. |
| 2007/0049898 A1 | 3/2007 | Hopkins et al. |
| 2007/0060926 A1 | 3/2007 | Escaf |
| 2007/0073214 A1 | 3/2007 | Dacquay et al. |
| 2007/0073309 A1 | 3/2007 | Kadziauskas et al. |
| 2007/0078379 A1 | 4/2007 | Boukhny et al. |
| 2007/0085611 A1 | 4/2007 | Gerry et al. |
| 2007/0107490 A1 | 5/2007 | Artsyukhovich et al. |
| 2007/0231205 A1 | 10/2007 | Williams et al. |
| 2007/0249942 A1 | 10/2007 | Salehi et al. |
| 2008/0033342 A1 | 2/2008 | Staggs |
| 2008/0066542 A1 | 3/2008 | Gao |
| 2008/0067046 A1 | 3/2008 | Dacquay et al. |
| 2008/0082040 A1 | 4/2008 | Kubler et al. |
| 2008/0112828 A1 | 5/2008 | Muri et al. |
| 2008/0114289 A1 | 5/2008 | Muri et al. |
| 2008/0114290 A1 | 5/2008 | King et al. |
| 2008/0114291 A1 | 5/2008 | Muri et al. |
| 2008/0114300 A1 | 5/2008 | Muri et al. |
| 2008/0114311 A1 | 5/2008 | Muri et al. |
| 2008/0114312 A1 | 5/2008 | Muri et al. |
| 2008/0114372 A1 | 5/2008 | Edwards et al. |
| 2008/0114387 A1 | 5/2008 | Hertweck et al. |
| 2008/0125695 A1 | 5/2008 | Hopkins et al. |
| 2008/0125697 A1 | 5/2008 | Gao |
| 2008/0125698 A1 | 5/2008 | Gerg et al. |
| 2008/0129695 A1 | 6/2008 | Li |
| 2008/0146989 A1 | 6/2008 | Zacharias |
| 2008/0243105 A1 | 10/2008 | Horvath |
| 2008/0262476 A1 | 10/2008 | Krause et al. |
| 2008/0281253 A1 | 11/2008 | Injev et al. |
| 2008/0294087 A1 | 11/2008 | Steen et al. |
| 2008/0312594 A1 | 12/2008 | Urich et al. |
| 2009/0005712 A1 | 1/2009 | Raney |
| 2009/0005789 A1 | 1/2009 | Charles |
| 2009/0048607 A1 | 2/2009 | Rockley |
| 2009/0124974 A1 | 5/2009 | Crank et al. |
| 2009/0163853 A1 | 6/2009 | Cull et al. |
| 2010/0036256 A1 | 2/2010 | Boukhny et al. |
| 2010/0069825 A1 | 3/2010 | Raney |
| 2010/0069828 A1 | 3/2010 | Steen et al. |
| 2010/0185150 A1 | 7/2010 | Zacharias |
| 2010/0225209 A1* | 9/2010 | Goldberg ............... A61B 34/30 312/209 |
| 2010/0249693 A1 | 9/2010 | Links |
| 2010/0280435 A1* | 11/2010 | Raney ................ A61F 9/00745 604/22 |
| 2011/0092887 A1* | 4/2011 | Wong .................... A61B 17/00 604/22 |
| 2011/0092924 A1 | 4/2011 | Wong et al. |
| 2011/0092962 A1 | 4/2011 | Ma et al. |
| 2011/0098721 A1* | 4/2011 | Tran ....................... H01H 21/26 606/130 |
| 2011/0160646 A1 | 6/2011 | Kadziauskas et al. |
| 2012/0065580 A1 | 3/2012 | Gerg et al. |
| 2012/0083800 A1 | 4/2012 | Andersohn |
| 2013/0072853 A1 | 3/2013 | Wong et al. |
| 2013/0245543 A1 | 9/2013 | Gerg et al. |
| 2013/0289475 A1 | 10/2013 | Muri et al. |
| 2013/0303978 A1 | 11/2013 | Ross |
| 2014/0378986 A1* | 12/2014 | Eastman ................ A61B 17/00 606/107 |

FOREIGN PATENT DOCUMENTS

| | | |
|---|---|---|
| EP | 56019 A1 | 7/1982 |
| EP | 424687 A1 | 5/1991 |
| EP | 619993 A1 | 10/1994 |
| EP | 1010437 A1 | 6/2000 |
| EP | 1072285 A1 | 1/2001 |
| EP | 1113562 A1 | 7/2001 |
| EP | 1310267 A2 | 5/2003 |
| EP | 1464310 A1 | 10/2004 |
| EP | 1469440 A2 | 10/2004 |
| EP | 1550406 A2 | 7/2005 |
| EP | 1704839 A1 | 9/2006 |
| EP | 1779879 A1 | 5/2007 |
| EP | 1787606 A1 | 5/2007 |
| EP | 1849443 A1 | 10/2007 |
| EP | 1849444 A1 | 10/2007 |
| EP | 1857128 A1 | 11/2007 |
| EP | 1867349 A1 | 12/2007 |
| EP | 1310267 B1 | 1/2008 |
| EP | 1873501 A1 | 1/2008 |

(56) References Cited

FOREIGN PATENT DOCUMENTS

| | | | |
|---|---|---|---|
| EP | 1900347 A1 | 3/2008 |
| EP | 1925274 A2 | 5/2008 |
| EP | 1867349 B1 | 11/2008 |
| ES | 2264369 A1 | 12/2006 |
| GB | 2230301 A | 10/1990 |
| GB | 2352887 A | 2/2001 |
| GB | 2438679 A | 12/2007 |
| JP | S5724482 A | 2/1982 |
| JP | S58167333 A | 10/1983 |
| JP | 2008188110 A | 8/2008 |
| WO | WO-9220310 A1 | 11/1992 |
| WO | WO-9315777 A2 | 8/1993 |
| WO | WO-9317729 A1 | 9/1993 |
| WO | WO-9324082 A1 | 12/1993 |
| WO | 9405346 A1 | 3/1994 |
| WO | WO-9632144 A1 | 10/1996 |
| WO | WO-9818507 A1 | 5/1998 |
| WO | WO-9917818 A1 | 4/1999 |
| WO | WO-0000096 A1 | 1/2000 |
| WO | WO-0070225 A1 | 11/2000 |
| WO | WO-0122696 A1 | 3/2001 |
| WO | WO-0228449 A2 | 4/2002 |
| WO | WO-0234314 A1 | 5/2002 |
| WO | WO-03102878 A1 | 12/2003 |
| WO | WO-2004096360 A1 | 11/2004 |
| WO | WO-2004114180 A1 | 12/2004 |
| WO | WO-2005084728 A2 | 9/2005 |
| WO | WO-2005092023 A2 | 10/2005 |
| WO | WO-2005092047 A2 | 10/2005 |
| WO | WO-2006101908 A2 | 9/2006 |
| WO | WO-2006125280 A1 | 11/2006 |
| WO | WO-2007121144 A1 | 10/2007 |
| WO | WO-2007143677 A2 | 12/2007 |
| WO | WO-2007143797 A1 | 12/2007 |
| WO | WO-2007149637 A2 | 12/2007 |
| WO | WO-2008030872 A1 | 3/2008 |
| WO | WO-2008060859 A1 | 5/2008 |
| WO | WO-2008060902 A1 | 5/2008 |
| WO | WO-2008060995 A1 | 5/2008 |
| WO | WO-2010054146 A1 | 5/2010 |
| WO | WO-2010054225 A2 | 5/2010 |
| WO | 2013142009 A1 | 9/2013 |

OTHER PUBLICATIONS

Boyd, "Preparing for the Transition" in: The Art and Science of Cataract Surgery, Chapter 7, 2001, pp. 93-133.
Co-pending U.S. Appl. No. 13/922,475, filed Jun. 20, 2013.
Definition of "Parameter", Retrieved from the Internet:< URL: http://dictionary.reference.com/browse/parameter>.
English Human Translation of JP57024482 from Feb. 9, 1982.
European Search Report for Application No. EP10164058, dated Jun. 25, 2010, 2 pages.
European Search Report for Application No. EP13184138.9, dated Oct. 24, 2013, 7 pages.
Examination Report dated Mar. 28, 2012 for European Application No. EP09791072 filed Jul. 31, 2009, 3 pages.
International Preliminary Report on Patentability and Written Opinion for Application No. PCT/US07/083875, dated May 12, 2009, 8 pages.
International Preliminary Report on Patentability and Written Opinion for Application No. PCT/US07/083880, dated May 12, 2009, 7 pages.
International Preliminary Report on Patentability and Written Opinion for Application No. PCT/US07/084157, dated May 12, 2009, 10 pages.
International Preliminary Report on Patentability and Written Opinion for Application No. PCT/US07/084163, dated May 12, 2009, 8 pages.
International Preliminary Report on Patentability and Written Opinion for Application No. PCT/US08/064240, dated Nov. 24, 2009, 7 pages.
International Preliminary Report on Patentability and Written Opinion for Application No. PCT/US2006/38978, dated Apr. 16, 2008, 8 pages.
International Preliminary Report on Patentability and Written Opinion for Application No. PCT/US2006/39868, dated Apr. 16, 2008, 6 pages.
International Preliminary Report on Patentability and Written Opinion for Application No. PCT/US2008/072974, dated Feb. 16, 2010, 6 pages.
International Preliminary Report on Patentability and Written Opinion for Application No. PCT/US2008/71704, dated Feb. 2, 2010, 8 pages.
International Preliminary Report on Patentability and Written Opinion for Application No. PCT/US2009/052473, dated Feb. 1, 2011, 7 pages.
International Preliminary Report on Patentability and Written Opinion for Application No. PCT/US2009/063479, dated May 10, 2011, 11 pages.
International Preliminary Report on Patentability and Written Opinion for Application No. PCT/US2009/063589, dated May 10, 2011, 12 pages.
International Search Report and Written Opinion, dated Mar. 2, 2010, and International Preliminary Report on Patentability, dated May 10, 2011, for Application No. PCT/US2009/063482, 13 pages.
International Search Report and Written Opinion, dated Nov. 2, 2009, and International Preliminary Report on Patentability, dated Feb. 1, 2011, for Application No. PCT/US2009/052466, 12 pages.
International Search Report and Written Opinion, dated May 10, 2010, and International Preliminary Report on Patentability, dated May 10, 2011, for Application No. PCT/US2009/063569, 17 pages.
International Search Report and Written Opinion, dated Feb. 11, 2010, and International Preliminary Report on Patentability, dated May 10, 2011, for Application No. PCT/US2009/063486, 13 pages.
International Search Report and Written Opinion, dated Feb. 19, 2010, and International Preliminary Report on Patentability, dated May 10, 2011, for Application No. PCT/US2009/63488, 9 pages.
International Search Report and Written Opinion, dated Apr. 22, 2010, and International Preliminary Report on Patentability, dated May 10, 2011, for Application No. PCT/US2009/063493, 8 pages.
International Search Report for Application No. PCT/US07/083875, dated May 7, 2008, 4 pages.
International Search Report for Application No. PCT/US07/083880, dated May 30, 2008, 4 pages.
International Search Report for Application No. PCT/US07/084157, dated Apr. 1, 2008, 3 pages.
International Search Report for Application No. PCT/US07/084163, dated Apr. 1, 2008, 3 pages.
International Search Report for Application No. PCT/US08/064240, dated Oct. 29, 2008, 3 pages.
International Search Report for Application No. PCT/US08/071704, dated Nov. 26, 2008, 3 pages.
International Search Report for Application No. PCT/US08/072974, dated Feb. 23, 2009, 2 pages.
International Search Report for Application No. PCT/US2006/38978, dated Feb. 27, 2007, 3 pages.
International Search Report for Application No. PCT/US2006/39868, dated Nov. 12, 2007, 3 pages.
International Search Report for Application No. PCT/US2009/052473, dated Nov. 2, 2009, 3 pages.
International Search Report for Application No. PCT/US2009/063479, dated Jun. 11, 2010, 5 pages.
International Search Report for Application No. PCT/US2009/063589, dated Jul. 21, 2010, 7 pages.
International Search Report for Application No. PCT/US2013/027728, dated Jul. 31, 2013, 9 pages.
Merritt R., et al., Wireless Nets Starting to link Medical Gear [online] 2004 [retrieved on Feb. 12, 2007]. Retrieved from the Internet: <http://WWW.embedded.com/news/embeddedindustry/17200577?_requestid=174370>.

(56) References Cited

OTHER PUBLICATIONS

Phacoemulsification, [online] [retrieved on Jul. 1, 2009]. Retrieved from the Internet: <http://en.wikipedia.org/wiki/Phacoemulsification>, 2 pages.

* cited by examiner

MULTIFUNCTION FOOT PEDAL

CROSS-REFERENCE TO RELATED APPLICATIONS

This application claim priority to and is a continuation-in-part of U.S. patent application Ser. No. 12/613,591, filed Nov. 6, 2009, entitled Method For Programming Foot Pedal Settings and Controlling Performance Through Foot Pedal Variation, which claims priority to U.S. Provisional Patent Application Ser. No. 61/112,517, filed Nov. 7, 2008, the entireties of which are expressly incorporated herein by reference. This application also claims priority to U.S. Provisional Patent Application Ser. No. 61/983,324, filed Apr. 23, 2014, entitled System and Apparatus for Switch and Foot Pedal Tap Detection Filtering, the entirety of which is expressly incorporated herein by reference.

FIELD OF THE INVENTION

The present disclosure relates generally to foot pedal-operated controls, particularly for controlling surgical apparatuses.

DESCRIPTION OF RELATED ART

Surgical apparatuses often include operating controls for regulating settings or functions of the apparatus. Numerous types of apparatuses include a part in the form of a hand-held electrically operated medical implement or tool, commonly referred to as a handpiece. Operation of the apparatus requires control of various operating settings or functions required to use the handpiece. Such apparatus may include a control cabinet, power supply, one or more pumps, motors, and the like, as well as associated electronic hardware. For example, a surgeon may use such an apparatus during eye surgery in order to sonically emulsify eye tissue, irrigate the eye with a saline solution, and aspirate the emulsified lens from the eye.

Because the surgeon's hands are engaged in handling the handpiece during surgery, foot controls are often provided to control various operations of the associated apparatus, sometimes in the form of a foot pedal. Foot pedals vary in design, but traditional designs incorporate one or more electro-mechanical switches to allow the surgeon to initiate various system control functions using the foot pedal. This is a convenient mechanism for the surgeon, since it does not rely upon another person such as a scrub tech or nurse to initiate these control functions, for example via a graphical user interface (GUI) on a main console of the apparatus.

However, electro-mechanical switches introduce a variety of issues. For example, a foot pedals incorporating a plurality of physical switches can complicate the design of the foot pedal, increase its cost, and increase the potential for failure of a switch. Further, the placement of the switches may be less than optimal for a particular user, and cannot be modified or adapted to accommodate the user. This can decrease their effectiveness and can create issues with ergonomics and the like. Moreover, the switches are typically uncovered, and may become fouled by saline solution or other debris that gets into the foot pedal, potentially resulting in failure or reduction in the life of components within the foot pedal.

Improved foot pedal control systems, such as that described in U.S. Pat. No. 4,983,901 provide for a virtually unlimited number of control variations and modes for operating phacoemulsification apparatuses. Additional single linear and dual linear foot pedal patents include U.S. Pat. Nos. 5,268,624; 5,342,293; 6,260,434; 6,360,630; 6,452,120; 6,452,123; and 6,674,030.

However, despite the output from such foot pedals in regulating or controlling the apparatus, the pedal must be user friendly in order to provide a surgeon comfort and reliability in its use so as not to initiate disruption of the surgeon's concentration when performing surgery.

As may be expected, there are many types of foot pedals, but no common way to program the settings that are available for each type. Currently there are static graphical screens that when a user presses a button on the display screen they are presented with menus to select different options to be programmed into the foot pedal; however, until the present invention there was no interface between the foot pedal and the display screen to assist in setting the appropriate options for the user.

Prior art foot pedals employ a variety of side, top, toe, and heel switches to allow a surgeon to control a variety of apparatus functions. For example in ocular surgery, such functions can include Reflux, CASE Up, CASE Down, IV Pole Up, IV Pole Down, Next Major Mode, Previous Major Mode, Next Submode, Previous Submode, Next Active Mode, Previous Active Mode, Toggle Continuous Irrigation, Single Cut Vitrectomy, and the like. The foot pedal switches may be controlled by software, which may be configured using a computer-based GUI, for example. In a given configuration, foot pedal switch operations are relayed to the host software and translated into the corresponding configured function.

Thus, it is desirable to have a unified interface for achieving an intuitive way of programming any type of foot pedal attached to a system, wherein the interface is graphical in nature and can receive feedback from the foot pedal and display the information in real time on a display screen. The present invention fulfills that need.

Additionally, there is a need to immediately access multiple pre-programmed memory settings during a surgical procedure. For example, during a phacoemulsification procedure, the surgeon may need or want to switch between multiple pre-programmed memory settings to address issues arising during surgery, such as different lens densities, different situations, and/or different portion of the surgery, e.g. initiation of emulsification vs. cleaning/polishing the capsule. Prior to the present invention, the surgery had to be halted until the surgeon or user could complete the change. Thus, it is desirable to have a mechanism for accessing multiple pre-programmed memory settings and the present invention fulfills that need.

SUMMARY

An illustrative embodiment includes a method of using a foot pedal to select multiple pre-programmed settings, comprising selecting a direction of movement of a treadle of the foot pedal, wherein the direction is selected from the group consisting of pitch and yaw; and moving the treadle in the selected direction to one or more selected from the group consisting of: a first location, wherein the first location is a first pre-programmed setting; a second location, wherein the second location is a second pre-programmed setting; and a third location, wherein the third location is a third pre-programmed setting.

In an embodiment of the present invention, a foot pedal comprises a treadle, wherein the treadle is capable of moving in at least one direction selected from the group consisting of pitch and yaw, and wherein at least one of the directional movements of the treadle is capable of acting as a switch.

Other features and advantages of the disclosed surgical control devices and methods should be apparent from the following description of exemplary embodiments, which illustrate, by way of example, aspects of various embodiments.

DETAILED DESCRIPTION

Figure 1:
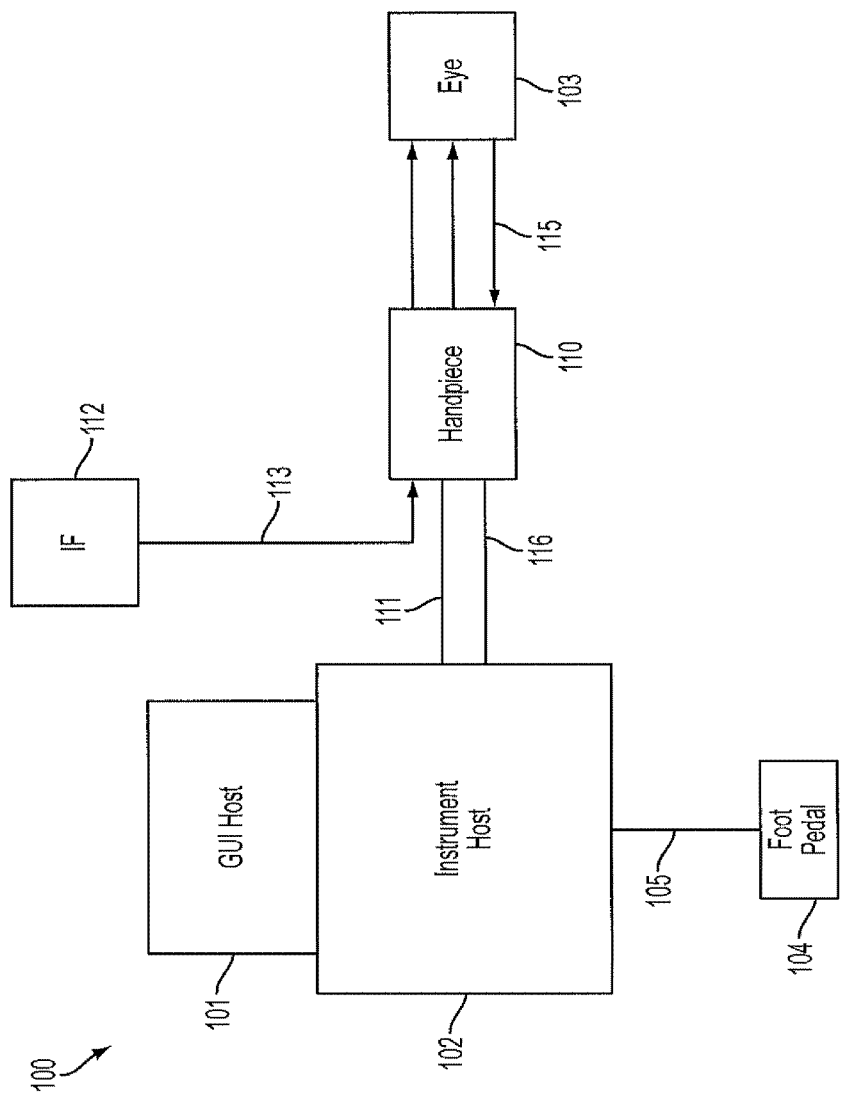
FIG. 1 is a functional block diagram of an exemplary phacoemulsification system.

The following description and the drawings illustrate specific embodiments sufficiently to enable those skilled in the art to practice the described system and method. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

In an embodiment, the functionality provided by electromechanical switches is produced instead by using the pitch of the foot pedal treadle in the vertical direction, or the yaw of the foot pedal treadle in the horizontal direction, or both. Such an embodiment allows for, but does not require, the elimination of the electromechanical switches and the simplification of the foot pedal hardware design. In an embodiment, a feedback signal may be provided to the user indicating the state of the pedal has been changed, such as an audible signal, a vibration signal, a visual signal such as a flashing light or an indicator on the GUI, or combinations of these.

A plurality of different conditions of the treadle may be used to define state changes in the foot pedal. Such conditions may include, for example, a pivotably movable treadle that can pivot in a vertical direction about a horizontal axis, called pitch, or in a horizontal direction about a vertical axis, called yaw, or both. In either case, the angle of pitch and/or yaw may be recognized as defined states or as points of transition from one state to another. The maximums of the ranges of motion may also be recognized, such as the top and/or bottom of the pedal's pitch, or the maximum left and/or right yaw. In addition, a particular speed and extent of motion, such as a tap or stomp of the pedal, may be recognized. Furthermore, a duration of maintaining a pedal position may also be recognized, such as pressing a pedal for a couple of seconds and releasing it to turn a feature on or off. Such foot pedal states and/or state changes may be used to define a plurality of virtual switches. That is, the operation of a plurality of physical switches may be mimicked by a corresponding plurality of states or state changes of a single foot pedal treadle. The states or state changes of the treadle are used to define a plurality of virtual switches.

In embodiments, the pitch, or angle of incline, of the treadle from a reference position such as horizontal, and/or the yaw of the treadle from a reference position such as a center of a range of horizontal movement, can be used to define a plurality of zones. For example, a plurality of zones may be defined, each zone existing between two different angles of pitch or yaw. Such zones may be defined to be active or passive. For example, a plurality of active zones may be configured to be adjacent to each other, or alternatively two active zones may be separated by an inactive zone.

In embodiments, virtual switches can be used in conjunction with one or more physical switches. For example, one of a plurality of physical switches on or coupled to a foot pedal with a movable treadle may be used to turn on or off the virtual switch functionality of a foot pedal having predefined virtual switches.

In an alternative embodiment, a foot pedal tap may enter the mode where the user can control virtual switches based upon pitch or yaw. Once the foot pedal is in the "virtual switch on" mode, moving the foot pedal to a predefined state, such as into one of a plurality of defined foot pedal zones, may activate the corresponding virtual switch. The activation may be confirmed by a visual, audible, or haptic signal to provide feedback to the user.

In an embodiment, the pitch range of motion of a foot pedal treadle may be divided into four zones, with a dead-band at the top and bottom of the foot pedal travel range. When released, the treadle settles at a default position, such as toward the top of the range, when it is fully released. In another embodiment, the yaw range of motion of a foot pedal treadle may also be divided into four zones, with a dead-band at the left and right ends of the foot pedal travel range. When released, the treadle will settle at default position, such as the center of the range.

In embodiments, there are two primary types of system control functions. One of these is the toggling of discrete functions, such as turning on and off a continuous flow of irrigation fluid. The other primary type includes press-and-hold functions, such as raising and lowering an IV pole to a desired height. Both types of functions can be controlled using virtual switches.

In an embodiment, to turn a function on and off in toggle mode, the user may press the pedal treadle to a selected switch zone, and then quickly release the pedal. For example, if foot pedal pitch zone 1 is defined as controlling irrigation fluid, the user may move the treadle into pitch zone 1 and quickly release it. The first such movement may turn irrigation on, and a second such movement may turn irrigation off.

In an embodiment, to turn a function on and off in press-and-hold mode, such as adjusting the height of the IV pole, mode activation occurs when the user holds the treadle in a specific switch zone for at least a defined amount of time, for example, for at least two seconds. The switch zone will then remain active until the user moves the pedal out of that specific switch zone.

In an embodiment, to exit a virtual switch on pitch mode, the user may press the foot pedal treadle all the way down to its full travel position and hold it there for a predetermined duration, for example, for two seconds. Thereby, the mode is ended, which may be confirmed by one or more of an audible or haptic signal to the user or a visual indicator on the GUI. The user can then return the foot pedal to its default "zero" position to return to normal, non-virtual switch foot pedal operation. In an embodiment, the predetermined duration may be configurable.

Similarly, to exit a virtual switch on yaw mode, the user may push the foot pedal treadle all the way to its right or left to the full extent of travel and hold for a predetermined, and possibly configurable, duration. Thereby, the mode is ended, which may be confirmed by one or more of an audible or haptic signal to the user or a visual indicator on the GUI. The user can then return the foot pedal to its default "zero" position to return to normal, non-virtual switch foot pedal operation.

In an embodiment, the previously described exit from virtual switch on pitch or yaw procedure can act as a means for canceling or exiting from a switch activation procedure, without completing any switch activations.

In an embodiment, the tap to enter the virtual switch on pitch mode may be defined as a quick transition from a first to a second pedal position, and back to the first. For example the foot pedal range of motion may be partitioned into four different zones FP0, FP1, FP2, and FP3, corresponding to virtual switches SW0, SW1, SW2 and SW3. Each switch may be configured for a specific function, or may also be disabled, for example via configuration software running on GUI host 101 or instrument host 102. Though these switch positions may correspond to the standard foot pedal positions FP0, FP1, FP2, and FP3, the switch zones could be configured independently as well. For example, the pedal may be programmed to have functionality that does not correspond to the standard foot pedal positions, and/or may be programmed with more or fewer pitch zones.

In an exemplary illustration, the switches are configured as SW0=IV Pole Down, SW1=IV Pole Up, SW2=Previous Major Mode, and SW3=Next Major Mode; and the user is a surgeon. In an exemplary operation, the surgeon enters the virtual switch on pitch mode by pressing the foot pedal into the SW0 zone for a predetermined duration. This action causes the pedal to enter the switch on pitch mode, which is confirmed by an audible or haptic feedback and display on the GUI. Upon staying in the SW0 zone for the predetermined time, an IV Pole Down command is sent to the IV pole and it starts lowering. Any transition out of the SW0 zone results in an IV Pole Stop command being sent to the IV pole, halting its downward motion. Had the surgeon held the pedal in the SW1 zone instead of the SW0 zone, the surgeon would have received distinctive feedback sufficient to identify the zone as SW1, such as 2 distinct audible or vibration feedback signals for example. Upon holding the pedal in the SW1 position for the predetermined duration, an IV Pole Up command is sent to the IV pole and it starts rising. Any transition out of the SW1 zone results in an IV Pole Stop command being sent to the IV pole, halting its upward motion.

If the surgeon proceeds into the SW2 zone and quickly releases to the FP0 position, this is interpreted by the instrument host 102 as activation of virtual switch SW2. Since SW2 is configured as Previous Major Mode in this illustration, the system would transition backward to the previous major mode available in the system. Similarly, moving the pedal into the SW3 zone would result in proceeding to the next major mode available in the system. At any time during operation of the pedal in the switch on pitch mode, pressing and holding the foot pedal treadle at full travel for a predetermined time results in exiting the switch on pitch mode, and returning to standard pedal operation.

Similarly, in a switch on yaw mode illustrative example, the foot pedal may be partitioned in switch zones that are laid out from left to right. For this example SW0 and SW1 are defined to be to the right of a center default pedal position or dead-band, and SW2 and SW3 to the right. The functionality of the virtual switch on yaw example operates similarly with regard to the switch behavior. One difference is the zero may be the center dead-band reference instead of toward a limit of motion. From the switch on yaw mode of operation, holding the pedal for a predetermined duration in one of the dead-bands at the left and right limit of the yaw travel range would exit the switch on yaw mode.

Other embodiments combine switching on pitch and/or yaw modes with any desired number of electro-mechanical switches. Any convenient number and location of electro mechanical switches may be implemented on or with a pedal or other controller that provides virtual switches based on the position of a control element. Combining electro mechanical switches with the virtual switch on pitch or yaw functionality offers a great number of possibilities.

Although the primary exemplary embodiments use a foot pedal pitch or yaw, analogous embodiments may be implemented using any control, such as a twist knob or lever, which provides angular data for control purposes. Any type of lever, twist dial, foot pedal, or the like used in any industry or other control context may benefit from this approach. Such controls might be a throttle lever on a vehicle, or a twist knob on an instrument control panel, or a foot pedal used with a musical instrument or a sewing machine, for example.

Embodiments of foot pedal control systems and methods will be discussed herein with a particular emphasis on a medical or hospital environment in which an ocular surgeon practices. For example, an embodiment may be part of a phacoemulsification surgical system that comprises an integrated high-speed control module for a handpiece. The surgeon may set or adjust a vibration speed via the GUI or foot pedal to control a phacoemulsification handpiece.

Referring now to FIG. 1, a block diagram is shown illustrating an exemplary phacoemulsification system 100. In the exemplary system, GUI host 101 and instrument host 102 may be distinct components communicatively coupled, or may reside on a single-board computer and communicate through inter-process communication. Such components or computer comprise hardware, including at least a microprocessor and at least one data storage device, such as a hard drive or flash memory, random access memory (RAM), or the like. Instrument host 102 typically takes the form of a computational device in the arrangement shown, but other arrangements are possible. For example, an interface of instrument host 102 may be communicatively coupled to other locations, systems, subsystems, and modules within and/or external to the instrument host 102, for distribution of instrument sensor data, instrument settings, parameter information, and the like.

Foot pedal 104 is communicatively coupled through a wired or wireless communications port to instrument host 102, and transmits control signals relating to the foot pedal treadle's physical position, corresponding virtual switch position information, or both, to the instrument host. Instrument host 102 may store in its storage device a database of configuration parameter values, executable programs, other data, and the like. In the exemplary embodiment, the treadle position or corresponding virtual switch position information can be converted by the instrument host 102 into a programmed switch function which is controlled by modifying the incline and/or orientation of the treadle by the user, as will be described.

In the exemplary system, a phacoemulsification handpiece 110 includes a needle, and means for ultrasonically vibrating the needle such as a piezoelectric crystal. The instrument host 102 provides power via electrical connection 111 to handpiece 110. An irrigation fluid (IF) source 112 can be coupled via a tube or other fluid channel 113 to the handpiece to provide irrigation fluid to handpiece 110. The irrigation fluid and ultrasonic power are applied using handpiece 110 to a subject eye (not part of the system) represented by block 103. Aspiration is provided to eye 103 by a pump (not shown), such as a peristaltic pump and/or Venturi pump, via the instrument host 102, through lines 115 and 116. A surgeon/operator may control the operation of the handpiece using control elements disposed on any or all of the handpiece, the instrument host 102, the GUI host 101, and foot pedal 104.

Figure 2:
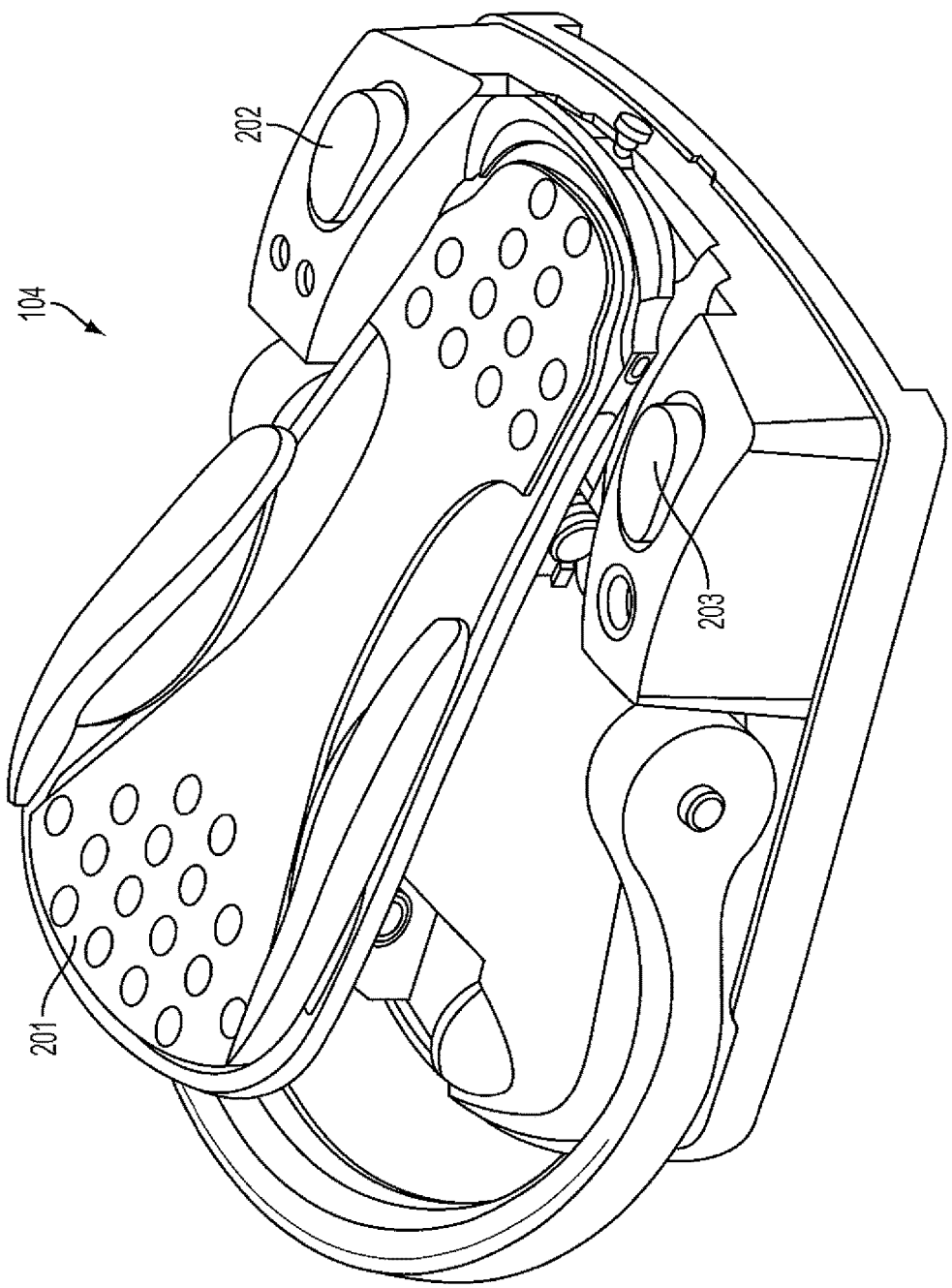
FIG. 2 illustrates an exemplary foot pedal.

FIG. 2 is an illustration of an exemplary foot pedal such as foot pedal 104. FIG. 2 shows treadle 201 and switches 202 and 203, although other switch and treadle configurations may be used. For example, switches may be placed on other parts of the foot pedal, or may be located apart from the pedal and coupled thereto, or may be entirely eliminated. An advantage of avoiding or minimizing the use of switches on the foot pedal is to avoid or minimize the number of components that may become fouled during ordinary use, and that may malfunction or fail as a result.

Figure 3:
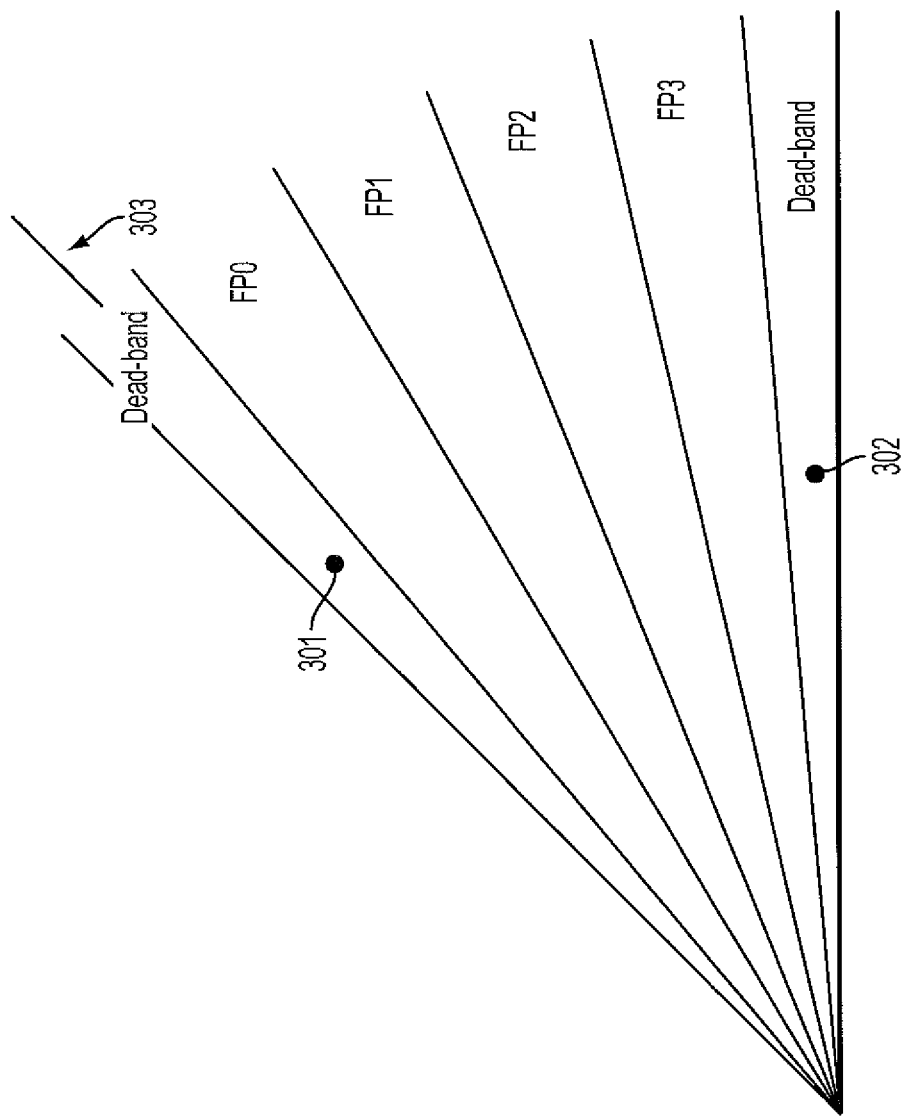
FIG. 3 illustrates a plurality of foot position zones in the pitch (up and down) direction for the treadle of an exemplary foot pedal.
Figure 4:
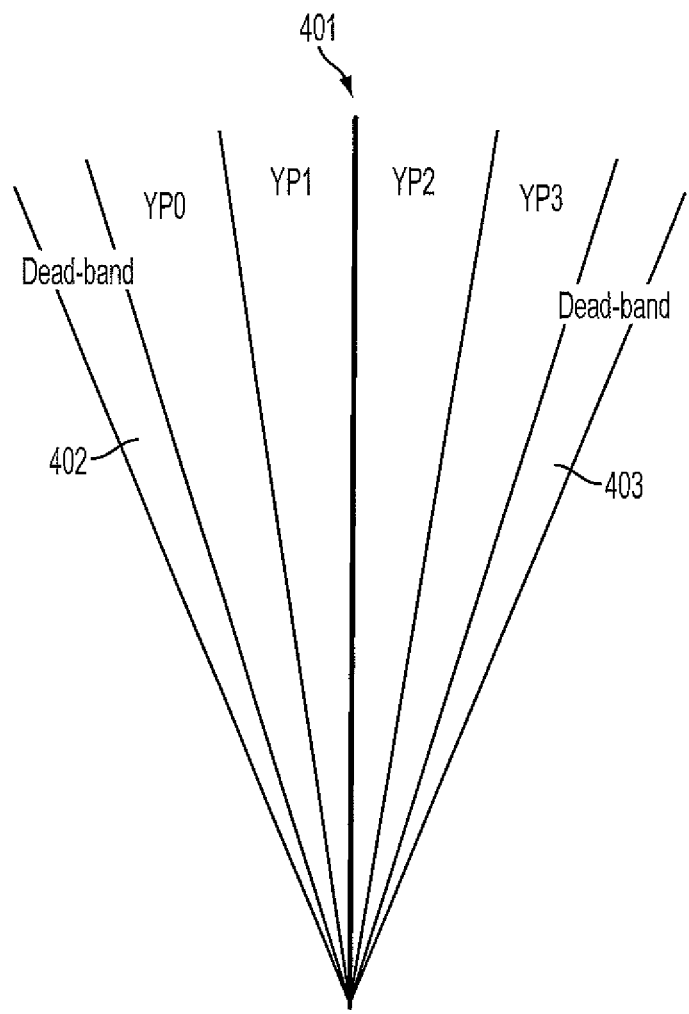
FIG. 4 illustrates a plurality of foot position zones in the yaw (side-to-side) direction for the treadle of an exemplary foot pedal.

As illustrated in FIG. 3, in an embodiment, the pitch range of motion of a foot pedal treadle may be divided into four zones, FP0, FP1, FP2, and FP3, corresponding to four virtual switches SW0, SW1, SW2, and SW3, respectively, with a dead-band 301, 302 at each end of the foot pedal travel range of pitch movement. The treadle settles at default position 303 when it is fully released. Although default position 303 is shown as being in the middle of dead-band 301, other default positions may be implemented. In an embodiment, the default pitch position may be configurable. The number of switch zones may also be configurable. Implementing more switch zones would give the user more options for control, while fewer switch zones would give the user more foot pedal travel between switch zones and easier control of the pedal's position. Similarly, as illustrated in FIG. 4, in an embodiment the yaw range of motion of a foot pedal treadle may be divided into four zones, YP0, YP1, YP2, and YP3, corresponding to four virtual switches SW0, SW1, SW2, and SW3, respectively, with a dead-band 402, 403 at each end of the foot pedal travel range. When released, the treadle settles at default position 401, which is shown in the center of the yaw range of motion, although other default positions may be implemented. As before, the default position, and/or the number of switch zones, may be configurable.

In an embodiment, the yaw directional movement configured to implement one or more virtual toggle switches, and the pitch directional movement configured to implement one or more virtual press-and-hold ("linear") controls, or vice versa. Partial virtual switch and partial virtual linear controls may be configured for either or both of the yaw directional movement and the pitch directional movement. Virtual linear controls may be configured for both yaw and pitch. Particular virtual switches may be configured for particular features, such as a first virtual switch for a first pump, a second virtual switch for a second pump, and a third virtual switch for irrigation. Any virtual switch may be paired with a linear control, for example using one of the yaw or pitch to select a particular function, and the other of the yaw or pitch to adjust the speed, intensity, or other variable of the particular function. Combinations of these features may also be configured.

Figure 5:
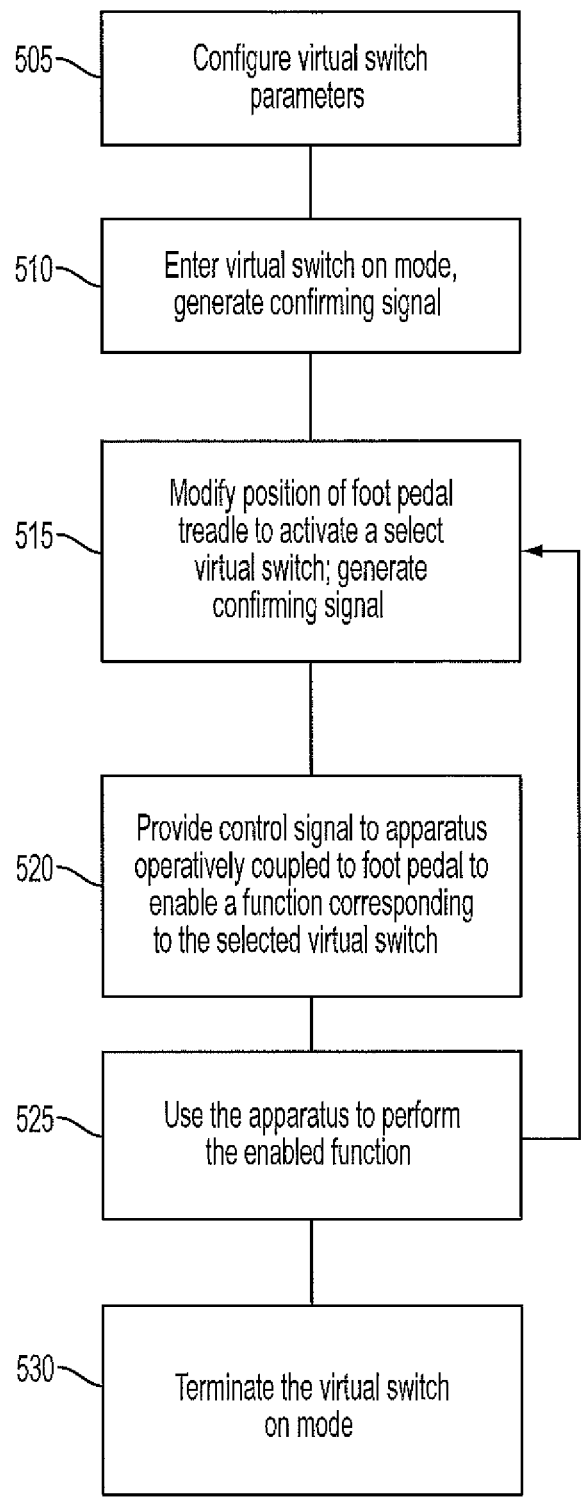
FIG. 5 is an exemplary operational flowchart.

FIG. 5 is a flowchart of an exemplary method of operation of the disclosed foot pedal that implements virtual switches. If one or more of the operational parameters of virtual switches implemented in a foot pedal with rotating treadle are configurable, the method begins at step 505 by configuring those parameters. For example, the various foot pedal position zones, time periods, and the like can be set. If the parameters are not configurable the method begins at step 510, or if they have already been set proceeds to step 510. At step 510, the user enters the virtual switch on mode, which may be confirmed with a feedback signal. Then the user modifies the position of the foot pedal treadle to activate a select virtual switch, 515, which may also be confirmed. For example, the user may adjust the treadle position to be within a select pitch zone, thereby activating the virtual switch that corresponds to that zone and enabling the corresponding function in apparatus that is operably coupled to the foot pedal. Activation of the virtual switch may be confirmed with a visual, audible, and/or haptic signal. A control signal is then provided to the apparatus, 520, which can then be used to perform the enabled function, 525. When complete, the user can modify the position of the treadle to activate a different virtual switch, returning to step 515 and proceeding from there. When the user has finished using the virtual switches, the user may terminate the virtual switch on mode, 530.

Figure 6:
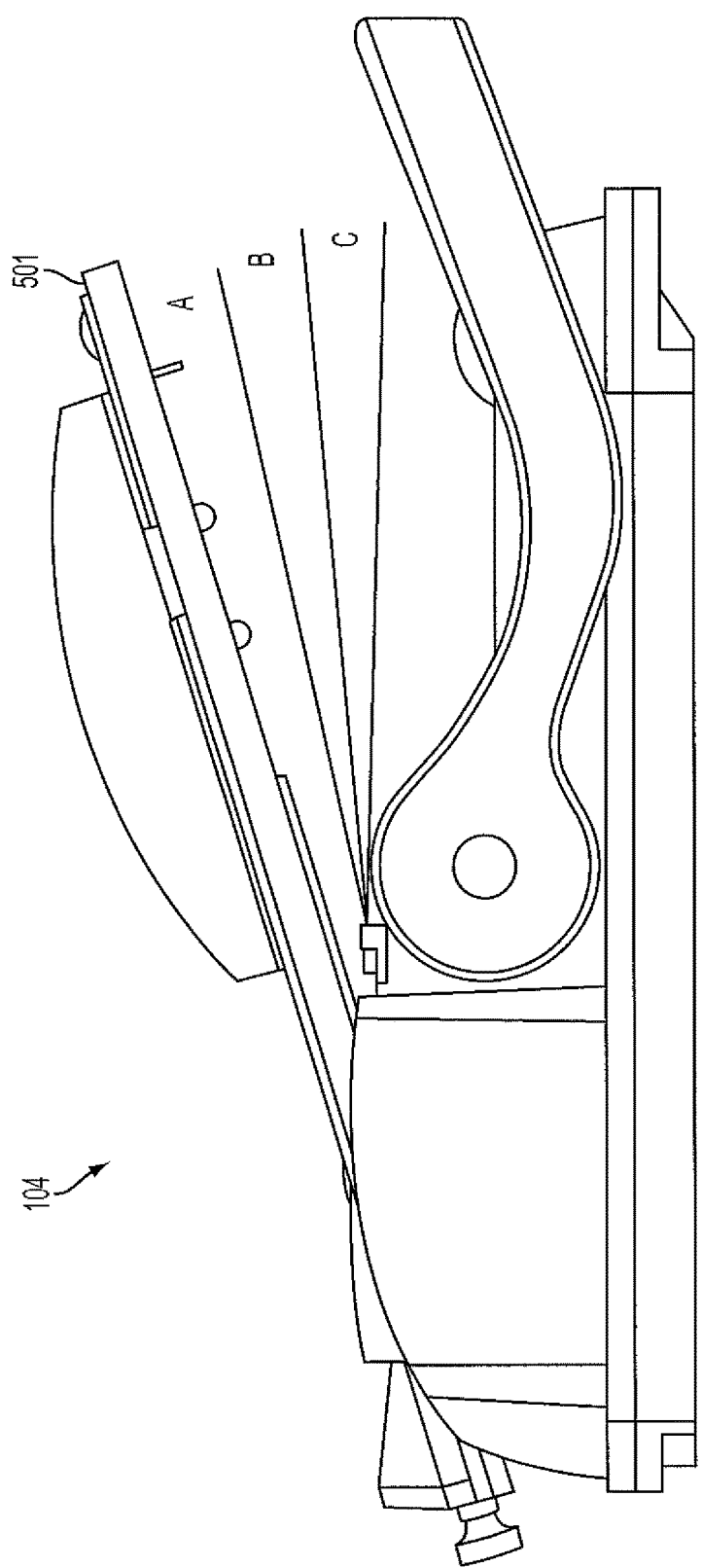
FIG. 6 is a profile view of a foot pedal showing the movement of a treadle in a pitch direction.
Figure 7:
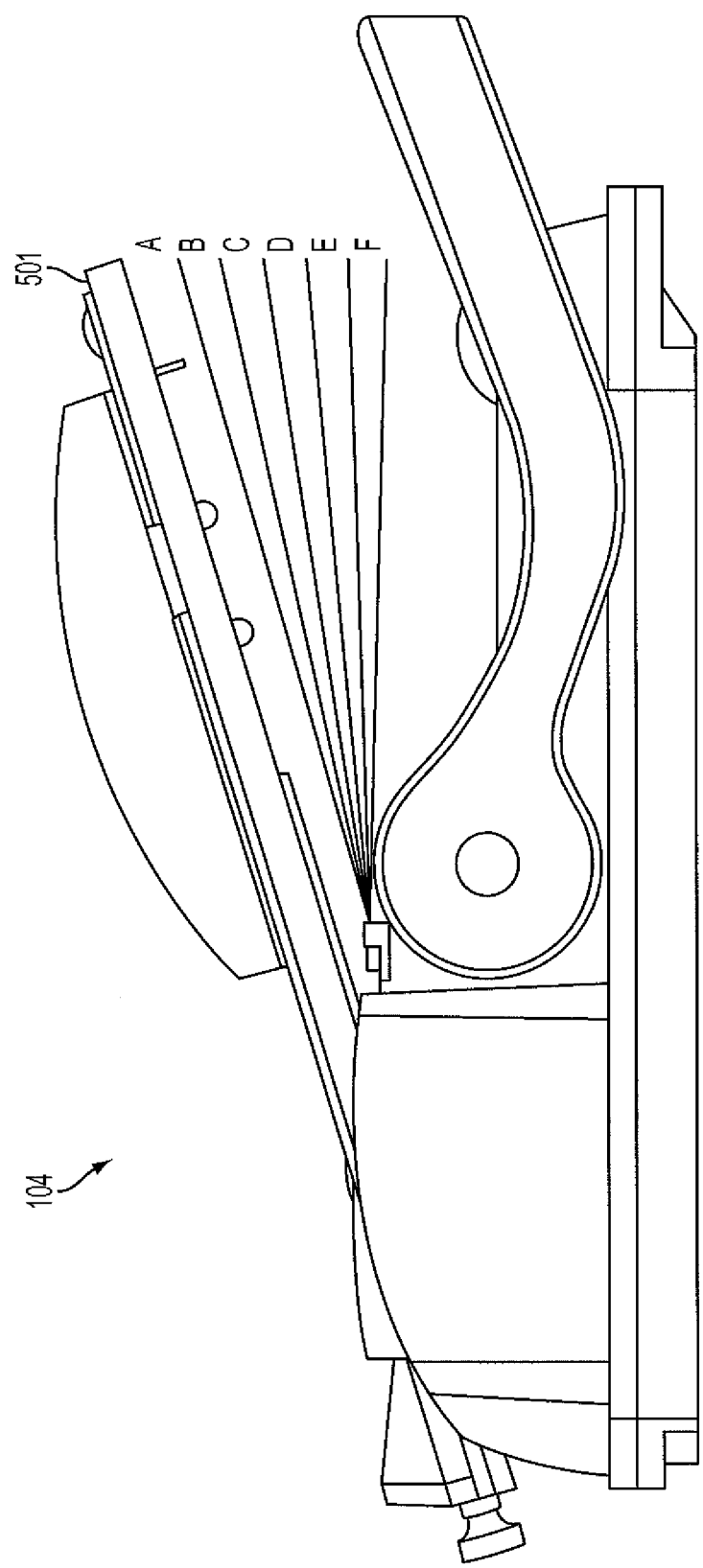
FIG. 7 is another profile view of a foot pedal showing the movement of a treadle in a pitch direction.

As shown in FIG. 6, in an exemplary embodiment a foot pedal 104 comprises a treadle 501 that moves in a pitch direction. As shown, the range of motion of treadle 501 is divided into three equal zones, A, B, and C. The pedal may be preconfigured to have only these three zones, or may be configurable to have a different number of zones, and/or zones that have configurable ranges. Pressing the pedal into one of the zones operates to select and activate a corresponding virtual switch, as described previously. The activation of a select switch can be confirmed by a feedback signal to the user, such as one or more of an audible, haptic, or visual signal as described previously. FIG. 7 shows the pedal 104, now configured to divide the pitch range of motion of treadle 501 into six zones A, B, C, D, E, and F.

Figure 8:
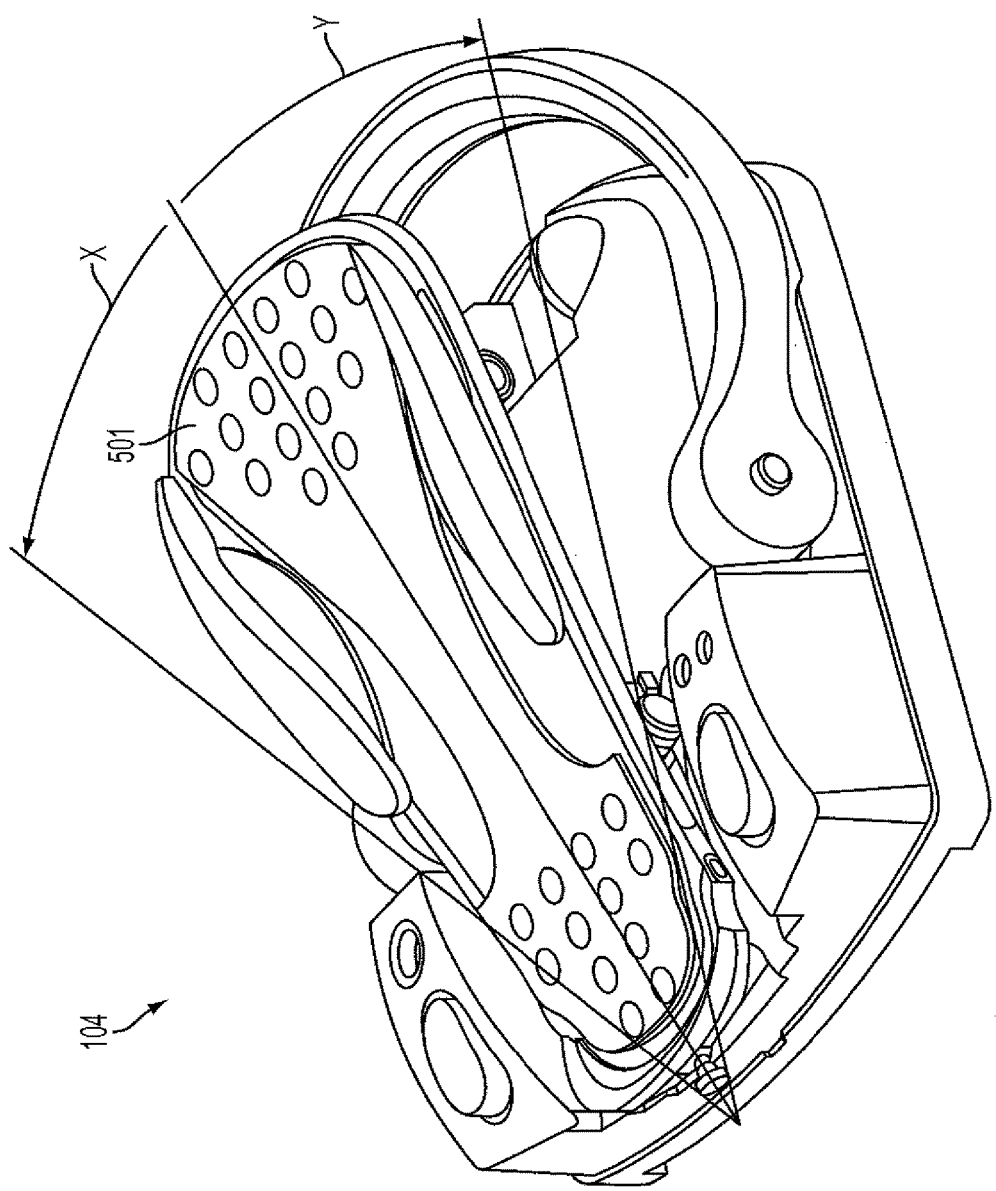
FIG. 8 is a perspective view of a foot pedal showing the movement of the treadle in a yaw direction.
Figure 9:
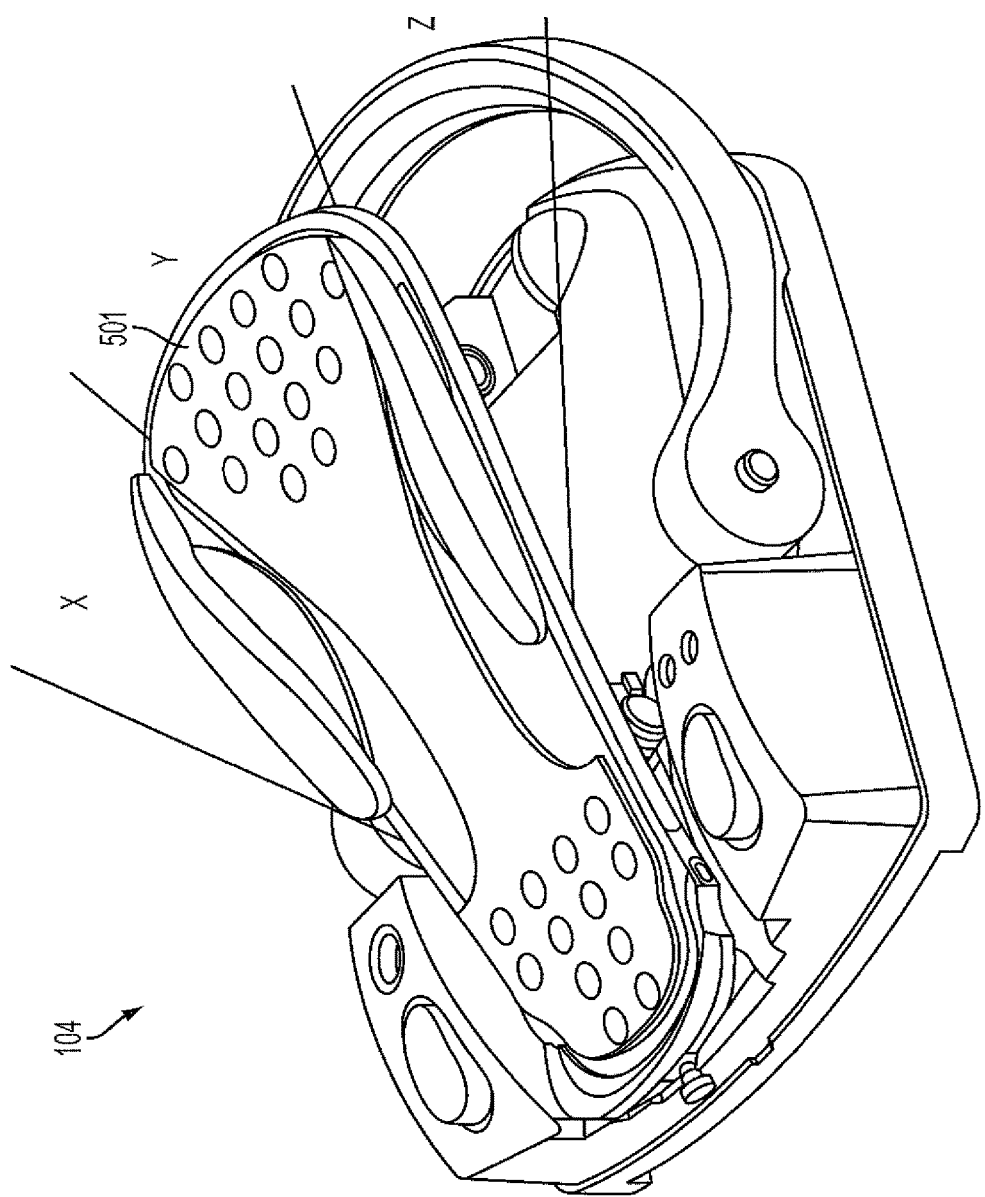
FIG. 9 is another perspective view of a foot pedal showing the movement of the treadle in a yaw direction.

FIG. 8 shows an exemplary pedal 104 with a treadle 501 able to move in a yaw direction. As shown, the range of motion of treadle 501 is divided into two equal zones, X and Y. The pedal may be preconfigured to have only these two yaw zones, or may be configurable to have a different number of zones, and/or zones that have configurable ranges. Turning the pedal into one of the zones operates to select and activate a corresponding virtual switch, as described previously. The activation of a select switch can be confirmed by a feedback signal to the user, such as one or more of an audible, haptic, or visual signal as described previously. FIG. 9 shows the pedal 104, now configured to divide the pitch range of motion of treadle 501 into three zones X, Y, and Z.

In an embodiment, a plurality of programmed settings may be saved as a set, such as a set of personal preferences of a particular user, and may be loaded into instrument host 102 to adapt the operation and functionality of the foot pedal to the user. In addition, a user may save different sets of programmed settings to use different surgical techniques, or to meet particular situations encountered during surgery, such as the density of a subject lens, intraoperative exigencies, and different parts of a procedure, such as sectioning, chopping, and/or polishing. In an embodiment, the user may change from a first set of programmed settings to a second set of settings by activating a particular electromechanical or virtual switch of the foot pedal.

In an embodiment, an ocular surgical apparatus can comprise an apparatus control device, such as a foot pedal communicatively coupled to an instrument host 102, configured to control at least one parameter of the apparatus. The instrument host 102 receives signals from the surgical control device, and evaluates the signals to implement one of a plurality of virtual switches or other virtual control mechanisms.

Unless otherwise indicated, the order of method steps described in connection with any embodiment may be varied without departing from the scope of the invention. Moreover, the various exemplary logical blocks, modules, circuits, algorithm steps, and the like described in connection with the disclosed embodiments may be implemented as electronic hardware, computer software executing on a computing device that includes at least a processor coupled to a memory device on which the software is stored, or combinations of both. Because of the various possible implementations, various illustrative components, blocks, modules, circuits, and steps may have been described herein generally in terms of their functionality. Whether such functionality is implemented in application specific hardware or in software executing on a general purpose computing device may depend, for example, upon the particular application and physical or cost constraints imposed on the overall system. Although the described functionality may be implemented in various ways for each application, the implementation decisions do not cause a departure from the scope of the present invention as set forth the claims.

In particular, the various illustrative logical blocks, modules, and circuits described in connection with the embodiments disclosed herein may be implemented or performed using a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, DOM memory, EPROM memory, EEPROM memory, registers, hard disk, a removable disk, a CD-ROM, or any other form of storage medium known in the art. An exemplary storage medium may be coupled to the processor such that the processor can read information from, and write information to, the storage medium. In the alternative, the storage medium may be integral to the processor. The processor and the storage medium may reside in an application specific integrated circuit (ASIC). The ASIC may reside in a user terminal. In the alternative, the processor and the storage medium may reside as discrete components in a user terminal.

The three traditional positions ("position" as used herein shall mean the disposition of a foot pedal treadle in a zone defined by a particular range of motion for a particular setting, e.g. irrigation) of the treadle in phacoemulsification include: position 1 for irrigation; position 2 for irrigation and aspiration; and position 3 for irrigation, aspiration, and ultrasonic power. When the foot pedal is in a resting position, there are no pumps running or ultrasonic power being exerted. Position 1 allows for irrigation of fluid to the eye from an irrigation source. The travel of the treadle within the first position may control the flow rate of fluid into the eye. Position 2 activates one or more pumps that are capable of increasing flow of fluid into and through the eye, aspirate fluid and lens material from the eye, and/or venting towards the eye to relieve pressure build up in the medical device system. The travel within position 2 may be programmed to control how the one or more pumps operate. For example, as the user continues to travel farther within a position, the aspiration rate may increase, the pump rate may increase, or the vacuum pressure may increase. Position 3 activates the ultrasound energy, which is used to help emulsify and/or break up the lens material. The travel within position 3 may be programmed to control, inter alia, how much power is exerted on the lens material, how the power is exerted (e.g. burst, pulse, etc.), and the length of time the power is on (duty cycle). With the present invention the user may move the treadle to various locations within the available degree of movement to set where each option begins and ends, as well as the type of control occurring within each beginning and ending, e.g., percent power distribution, type of pulses, vacuum level distribution, etc. The user may also set within a selected range of movement of the treadle how the particular programming setting will perform. For example, the ultrasonic power may increase linearly as the foot pedal is depressed or the power may increase at a set increment until a particular degree of travel of the treadle has been reached and then increments may become smaller or larger depending upon the user's preference.

For a dual action foot pedal, a user may program a pitch directional movement and/or a yaw directional movement to correspond to one or more settings. In an embodiment, to program a directional movement, a user selects either the pitch or the yaw directional movement of the treadle of the foot pedal by indicating the selection on a display screen, by moving the treadle in the selected directional movement, by activating a switch on the foot pedal itself, by voice command, or combinations thereof. Once the user has made a selection, the display screen will show all of the available programming settings for the selected directional movement. The available programming settings include, but are not limited to, irrigation and rate thereof, aspiration and rate thereof, choice of pump and control thereof, vacuum and control thereof, ultrasonic power and control thereof, and combinations thereof. Additional programming settings include use of a combination of pumps or switching between pumps; controlling the linear relationship between movement (travel of the treadle) and the programming setting; proportional relationship between movement and control of a programming setting (e.g. 5 mm (or 2°)=10 mmHg vs. 10 mm (or 4°)=100 mmHg; or 5 mm (or 2°)=10 Hz vs. 10 mm (or 4°)=100 Hz); and/or panel movement (constant rate within a particular zone or degree of movement of the treadle) of the programming settings. By pitching the foot pedal up and down, or yawing the foot pedal to the left and/or right, the user can modify the foot pedal and its degree of depression or yaw to correspond to a particular program setting. During configuration of the pedal, when a first designated position is reached, the user may indicate (confirm) the choice on the display screen or write in (save setting(s) in memory) the particular setting by any other mechanism described herein or known in the art, such as voice command and/or tap switch, and continue moving the foot pedal to a second designated location. When the second designated location is reached, the user may confirm the choice as a second setting. The user may continue until all of the desired and/or allowed settings for the directional movement of the foot pedal are set. When the dual linear foot pedal is used as described herein, it allows a user to control the functions, modes, and/or settings, simultaneously by using pitch, yaw, and combinations thereof. The interface may provide feedback to the user to confirm the settings for the pitch and/or yaw direction of the treadle.

Other mechanisms for setting and/or programming a particular setting may be employed including, but not limited to, clicking on an icon on a display screen using a mouse or touch screen, depressing a button or physical switch on a foot pedal, voice activated commands and/or combinations thereof.

The term "phacoemulsification" refers to a method of lens and cataract extraction from an eye. The procedure includes an ultrasonically vibrated needle which is inserted through a very small incision in the cornea in order to provide energy for emulsifying or breaking up of the lens and cataract which then can be aspirated and removed through the incision.

The term "diathermy" refers to a method of cautery to seal severed or ruptured blood vessels. Diathermy is used in ophthalmic surgery to halt bleeding associated with surgical incisions.

The term "vitrectomy surgery" refers to a method employed during cataract surgery when the posterior capsular bag has been broken and in the treatment of retinal detachments resulting from tears or holes in the retina. In cataract surgery, the same incision used for the phacoemulsification handpiece is used for inserting the vitrector to remove the vitreous gel. Vitrectomy surgery typically involves removal of vitreous gel and may utilize three small incisions in the pars plana of the patient's eye. These incisions allow the surgeon to pass three separate instruments into the patient's eye to affect the ocular procedure. The surgical instruments typically include a vitreous cutting device, an illumination source, and an infusion port.

The term "display" or "display screen" as used herein shall mean a graphical user interface (GUI), a screen, a monitor, touch screen, or any other device known in the art for displaying a visual picture or representation.

The previous description is provided to enable a person of ordinary skill in the pertinent arts to make or use the invention. Various modifications to the disclosed embodiments will be readily apparent to those skilled in the art, and the generic principles defined herein may be applied to other embodiments without departing from the spirit or scope of the invention. Thus, the present disclosure is not intended to be limited to the embodiments shown herein but is to be accorded the widest scope consistent with the principles and novel features disclosed herein.

According to an embodiment, upon attachment of a foot pedal to a medical device system, the interface of the system will recognize the type of foot pedal and the features of the foot pedal. A foot pedal may be attached to the medical device system by any mechanism known in the art, including, but not limited to, a wire connection and a wireless connection, e.g. Bluetooth® or IR. A display screen of the medical device system may present the user with a picture or representation of the foot pedal detected. The picture or representation may show all the switches and directional movements available for programming the attached foot pedal.

The invention claimed is:

1. A system for performing ocular surgery, comprising:
   a handpiece for performing surgical procedures;
   an instrument host coupled to the handpiece that includes:
     a data storage device configured for storing computer instructions;
     a processor communicatively coupled to the data storage device;
     a communications connection to the handpiece that provides operating instructions to the handpiece based on received control signals; and
     an electrical power connection to the handpiece that provides electrical power to the handpiece in accordance with the operating instructions; and
   a foot pedal communicatively coupled to the instrument host that provides the control signals, including:
     a base; and
     a treadle pivotably coupled to the base on at least one rotational axis;
     wherein the range of motion of the treadle as it pivots around the axis comprises a plurality of non-overlapping zones, each zone corresponding to a virtual switch that is activated when the treadle is oriented within that zone, by sending a respective one of the control signals to the instrument host, wherein prior to the virtual switch activation, the foot pedal is put into a virtual switch mode of operation by:
   tapping the treadle;
   wherein a tap for the tapping is defined by a predetermined extent of motion of the treadle, and one of a predetermined speed of the treadle and a predetermined amount of time the treadle is in a predetermined zone.

2. The system of claim 1, further comprising a feedback signal generator that generates a feedback signal when:
   a foot pedal operation activates or deactivates a virtual switch mode; or
   a foot pedal operation activates or deactivates a select virtual switch.

3. The system of claim 2, wherein the generated feedback signal is at least one selected from the group consisting of an audible signal, a haptic signal, and a visual signal.

4. The system of claim 2, wherein at least one of the generated signals corresponds to a particular predefined foot pedal operation.

5. The system of claim 1, wherein the treadle is able to pivot in one axis.

6. The system of claim 5, wherein the axis is horizontal, and the treadle angle of pitch is varied as it pivots about the axis.

7. The system of claim 5, wherein the axis is vertical, and the treadle angle of yaw is varied as it pivots about the axis.

8. The system of claim 1, wherein the treadle is able to pivot in at least a horizontal axis and a vertical axis, wherein:
   the treadle angle of pitch is varied as it pivots about the horizontal axis;
   the treadle angle of yaw is varied as it pivots about the vertical axis; and
   the treadle range of motion in both the pitch and yaw directions comprise a respective plurality of non-overlapping zones.

9. The system of claim 1, wherein the base comprises at least one electromechanical switch that is activated when pressed to send one of the control signals to the instrument host.

10. The system of claim 1, further comprising a graphical user interface (GUI) host communicatively coupled to the instrument host, the GUI host comprising a display device that presents information of at least one of the foot pedal and the handpiece.

11. A foot pedal for use in a system for performing ocular surgery, comprising:
a base;
a communications port included in the base for communicatively coupling the foot pedal to an instrument host, that provides control signals to the instrument host; and
a treadle pivotably coupled to the base on at least one rotational axis;
wherein the range of motion of the treadle as it pivots about the axis comprises a plurality of non-overlapping zones, each zone corresponding to a virtual switch that is activated when the treadle is oriented within that zone by sending a respective one of the control signals to the instrument host, wherein prior to the virtual switch activation, the foot pedal is put into a virtual switch mode of operation by:
tapping the treadle;
wherein a tap for the tapping is defined by a predetermined extent of motion of the treadle, and one of a predetermined speed of the treadle and a predetermined amount of time treadle is in a predetermined zone.

12. The foot pedal of claim 11, wherein the treadle is able to pivot about one axis.

13. The foot pedal of claim 12, wherein the axis is horizontal, and the treadle angle of pitch is varied as it pivots about the axis.

14. The foot pedal of claim 12, wherein the axis is vertical, and the treadle angle of yaw is varied as it pivots about the axis.

15. The foot pedal of claim 10, wherein the treadle is able to pivot about at least a horizontal axis and a vertical axis, wherein:
the treadle angle of pitch is varied as it pivots about the horizontal axis;
the treadle angle of yaw is varied as it pivots about the vertical axis; and
the treadle range of motion in both the pitch and yaw directions comprise a respective plurality of non-overlapping zones.

16. The foot pedal of claim 15, wherein the pitch direction is divided into four zones, and the yaw direction is divided into three zones.

17. The foot pedal of claim 15, wherein the plurality of zones are user configurable.

18. The foot pedal of claim 15, wherein information of the treadle angle of pitch, yaw, or both, defines a foot pedal state or a point of transition from one state to another.

19. The foot pedal of claim 15, wherein the treadle angle of pitch includes at least one of a top or bottom of the pedal's pitch range of motion, or a left or right limit of the pedal's yaw range of motion.

20. The foot pedal of claim 15, wherein the information of the treadle comprises a predetermined speed and extent of motion that defines a tap or stomp of the foot pedal.

21. The foot pedal of claim 15, wherein the information of the treadle comprises a duration of maintaining a treadle position.

22. The foot pedal of claim 21, wherein the information of the treadle comprises pressing the treadle into a predetermined position or zone for a predetermined amount of time and releasing it.

23. The foot pedal of claim 11, wherein the plurality of non-overlapping zones are defined from a horizontal pitch reference position or a midpoint of the yaw range of motion, each zone existing between two different angles of pitch or yaw.

24. The foot pedal of claim 23, wherein each zone is defined to be active or passive.

25. The foot pedal of claim 11, wherein the base comprises at least one electromechanical switch that is activated when pressed to send one of the control signals to the instrument host.

26. The foot pedal of claim 25, wherein one of the electromechanical switches toggles on or off a mode of foot pedal operation in which the virtual switches are operable.

27. A method of operating a system for performing ocular surgery, comprising:
modifying an angle of a treadle of a foot pedal operatively coupled to a handpiece to activate a predefined virtual switch function corresponding to a treadle position within a zone of treadle movement, the zone defined by a portion of a full range of motion of the treadle as it pivots about an axis of rotation; and
upon activation of the virtual switch, generating a feedback signal confirming the virtual switch has been activated;
providing a control signal to the handpiece based on an operation of the activated virtual switch; and
using the handpiece to perform a surgical procedure on a subject eye enabled by the control signal, wherein prior to the virtual switch activation, the foot pedal is put into a virtual switch mode of operation by:
tapping the treadle;
wherein a tap for the tapping is defined by a predetermined extent of motion of the treadle, and one of a predetermined speed of the treadle and a predetermined amount of time the treadle is in a predetermined zone.

28. The method of claim 27, wherein the zone is one of a plurality of zones.

29. The method of claim 27, wherein the axis is one of a horizontal axis and a vertical axis.

30. The method of claim 27, wherein:
the zone is one of a plurality of zones into which the range of motion of the treadle is divided, each zone corresponding to a different virtual switch, plus a dead-band adjacent to at least one maximum extent of the treadle travel range; and
when it is fully released, the treadle settles at a predefined default position.

31. The method of claim 30, wherein the range of motion is one of:
a pitch range of motion, wherein the maximum extent of the treadle travel range is one of the top and the bottom of the range, and the default position is within the dead-band at the top of the range; and
a yaw range of motion, wherein the maximum extent of the treadle travel range is one of the left side and the right side of the range, and the default position is at the center of the yaw range of motion.

32. The method of claim 27, wherein there are two primary types of system control functions, comprising a toggle function type in which the function turns on or off, and a press-and-hold function type in which the function remains active only as long as the treadle remains in the corresponding zone.

33. The method of claim 32, wherein the function type is a toggle function type, further comprising:

pressing the treadle to a selected switch zone to toggle the corresponding function on or off; and releasing the treadle within a predetermined amount of time defined as a short period.

34. The method of claim 32, wherein the function type is a press-and-hold function type, further comprising:

pushing the treadle in a select switch zone for at least a predetermined amount of time defined as a long period to instantiate the corresponding function; and moving the treadle out of the zone to terminate the instantiated function.

35. The method of claim 27, further comprising:

terminating the virtual switch mode by one of:

pushing the treadle all the way down to its full travel position and holding it there for a predetermined duration; and pushing the treadle all the way to its full travel position in the right or left direction and holding it there for a predetermined duration;

confirming the termination by generating at least one selected from the group consisting of a visual, audible, and haptic feedback signal; and returning the treadle to its default position to return to normal, non-virtual switch foot pedal operation.

36. The method of claim 35, wherein at least one of the short period, the long period, and the predetermined duration is configurable.

\* \* \* \* \*